US006420709B1

United States Patent
Block et al.

(10) Patent No.: US 6,420,709 B1
(45) Date of Patent: *Jul. 16, 2002

(54) METHODS OF MINIMIZING SCATTERING AND IMPROVING TISSUE SAMPLING IN NON-INVASIVE TESTING AND IMAGING

(75) Inventors: Myron J. Block, North Salem, NH (US); Lester Sodickson, Waban, MA (US)

(73) Assignee: Optix LP, Juniper Island, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/749,331

(22) Filed: Dec. 27, 2000

Related U.S. Application Data

(60) Division of application No. 09/406,675, filed on Sep. 27, 1999, now abandoned, which is a division of application No. 08/937,934, filed on Sep. 25, 1997, now Pat. No. 6,064,065, which is a division of application No. 08/479,955, filed on Jun. 7, 1995, now Pat. No. 5,672,875, which is a continuation-in-part of application No. 08/333,758, filed on Nov. 3, 1994, now Pat. No. 5,818,048, which is a continuation-in-part of application No. 08/182,572, filed on Jan. 14, 1994, now Pat. No. 5,424,545, which is a continuation-in-part of application No. 08/130,257, filed on Oct. 1, 1993, now Pat. No. 5,434,412, which is a continuation-in-part of application No. 07/914,926, filed on Jul. 17, 1992, now Pat. No. 5,334,287.

(51) Int. Cl.[7] .................................................. G01J 3/02
(52) U.S. Cl. ........................................ 250/343; 356/39
(58) Field of Search ................................ 250/343, 347, 250/341.1; 356/39; 128/633, 634

(56) References Cited

U.S. PATENT DOCUMENTS

| | | | |
|---|---|---|---|
| 4,555,179 A | 11/1985 | Langerholc et al. | ........ 356/342 |
| 4,776,340 A | 10/1988 | Moran et al. | ................ 128/634 |
| 5,028,787 A | 7/1991 | Rosenthal et al. | .......... 250/341 |
| 5,054,487 A | 10/1991 | Clarke | ......................... 128/633 |
| 5,321,265 A | 6/1994 | Block | .......................... 250/343 |
| 5,440,388 A | 8/1995 | Erickson | ...................... 356/346 |
| 5,450,193 A | 9/1995 | Carlesen et al. | ............. 356/301 |
| 5,522,388 A | 6/1996 | Ishikawa et al. | .............. 356/39 |
| 5,672,875 A * | 9/1997 | Block et al. | ................. 250/343 |
| 5,799,656 A * | 9/1998 | Alfano et al. | ............... 128/664 |
| 6,090,332 A * | 7/2000 | Marder et al. | ............... 264/435 |

OTHER PUBLICATIONS

Alfano, R.R., et al, "Time–Resolved Imaging of Translucent Droplets in Highly Scattering Turbid Media," *Science*, vol. 264, 1913–1915 (1994).

Anderson, G.E., et al., "Microscope Imaging Through Highly Scattering Media," *Optics Letters*, vol. 19, No. 13, 981–983 (1994).

Andersson–Engels, S., et al., "Multispectral Tissue Characterization With Time–Resoved Detection of Diffusely Scattered White Light," *Optics Letters*, vol. 18, No. 20, 1697–1699; (1993).

Benaron, D., "Optical Biopsy and Imaging Advance Medical Care," *Laser Focus World,* 79–83 (1994).

(List continued on next page.)

*Primary Examiner*—Georgia Epps
*Assistant Examiner*—Richard Hanig
(74) *Attorney, Agent, or Firm*—Lahive & Cockfield, LLP

(57) ABSTRACT

An improved method and apparatus for use in optical testing of concentration in samples has been developed. The apparatus restricts the solid angle of illumination and the solid angle of detection to eliminate a high proportion of the scattered radiation while allowing the ballistic radiation and the snake-like radiation to be transmitted. In samples which contain multiple scattering centers, this allows less correction for variations in effective pathlength and allows easier calibration of the apparatus. The use of polarized radiation as a means of minimizing scattered radiation in the sample is also disclosed.

10 Claims, 9 Drawing Sheets

OTHER PUBLICATIONS

Benaron, D. and Stevenson, D., "Optical Time–of–Flight and Absorbance Imaging of Biologic Media," *Science*, vol. 259, 1463–1466 (1993).

Burns, D., "Optical Tomography for Three–Dimensional Spectroscopy," *Applied Spectroscopy*, vol. 48, No. 5, 12A–19A (1994).

Cope, M. and Delpy, D.T., "System for Long–term Measurement of Cerebral Blood and Tissue Oxygenation on Newborn Infants by Near Infra–red Transillumination," *Medical & Biological Engineering & Computing*, 289–294 (1988).

Cope, M. et al., "Data Analysis Methods for Near Infrared Spectroscopy of Tissue: Problems in Determining the Relative Cytochrome $aa_3$ Concentration," *SPIE*, vol. 1431, 251–261 (1991).

Cope et al., "Methods of Quantitating Cerebral Near Infrared Spectroscopy Data," *Adv. Exp. Med. Biol.*, vol. 222, 183–190 (1988).

Das, B.B., "Ultrafast Time–gated Imaging in Thick Tissues: a Step Toward Optical Mammography," *Optics Letters*, vol. 18, No. 13, 1092–1094 (1993).

de Kock, J.P., and Tarassenko, L., "Pulse Oximetry: Theoretical and Experimental Models," *Med. Biol. Eng. Comp.*, vol. 31, 291–300 (1993).

Delpy, D.T., et al., "Estimation of Optical Pathlength Through Tissue From Direct Time of Flight Measurement," *Phys. Med. Biol.*, vol. 33, No. 12, 1433–1442 (1988).

Fine, I., and Weinreb, A., "Multiple–scattering Effects in Transmission Oximetry," *Med. Biol. Eng. Comp.*, vol. 31, 516–522 (1993).

Kohl, M., and Cope, M., "Influence of Glucose Concentration on Light Scattering in Tissue–simulating Phantoms," *Optics Letters*, vol. 19, No. 24, 2170–2172 (1994).

Kubelka, P., "New Contributions to the Optics of Intensely Light–Scattering Materials. Part II: Nonhomogeneous Layers," *J. Opt. Soc. America*, vol. 44, 330–335 (1954).

Maier, J., et al., "Possible Correlation Between Blood Glucose Concentration and the Reduce Scattering Coefficient of Tissues in the Near Infrared," *Optics Letters*, vol. 19, No. 24, 2062–2064 (1994).

Mendelson, Y., "Pulse Oximetry: Theory and Applications for Noninvasive Monitoring," *Clin. Chem.*, vol. 38, No. 9, 1601–1607 (1992).

Sanchez–Carrillo, C., et al., "Test of a Noninvasive Instrument for Measuring Hemoglobin Concentration," *Intl. J. Technol. Assess. Health Care*, vol. 5, No. 4, 659–666 (1989).

Schmitt, J., "Simple Photon Diffusion Analysis of the Effects of Multiple Scattering on Pulse Oximetry," *IEEE Trans. Eng.*, vol. 38, No. 12, 1194–1203 (1991).

Schmitt, J., et al., "Measurement of Blood Hematocrit by Dual–wavelength Near–IR Photoplethysmography," *SPIE*, vol. 1641, 150–161 (1992).

Sodickson, L., and Block, M., "Kromoscopic Anaylsis: A Possible Alternative to Spectroscopic Analysis for Noninvasive Measurement of Analytes In Vivo," *Clin. Chem.*, vol. 40, No. 9, 1838–1844 (1994).

Steuer, R.R., et al., "Clinical Evaluation of the Noninvasive Hematocrit Monitro," *Am. Clin. Lab.*, vol. 11, No. 5, 18–21 (1992).

Steuer, R.R., et al., "Evaluation of a Noninvasive Hematocrit Monitor: A New Technology," *Am. Clin. Lab.*, vol. 10, No. 6, 20–22 (1991).

Wist, A., et al., "Increased Spatial Resolution in Transillumination Using Collimated Light," *IEEE Transactions on Medical Imageing*, vol. 12, No. 4, 751–757 (1993).

Wukitsch, M., et al., "Pulse Oximetry: Analysis of Theory, Technology, and Practice," *J. Clin. Monit.*, vol. 4, No. 4, 290–301 (1988).

Wyatt, J.S. et al., "Measurement of Optical Path Length for Cerebral Near–Infrared Spectroscopy in Newborn Infants," *Dev. Neurosci.*, vol. 12, 140–144 (1990).

\* cited by examiner

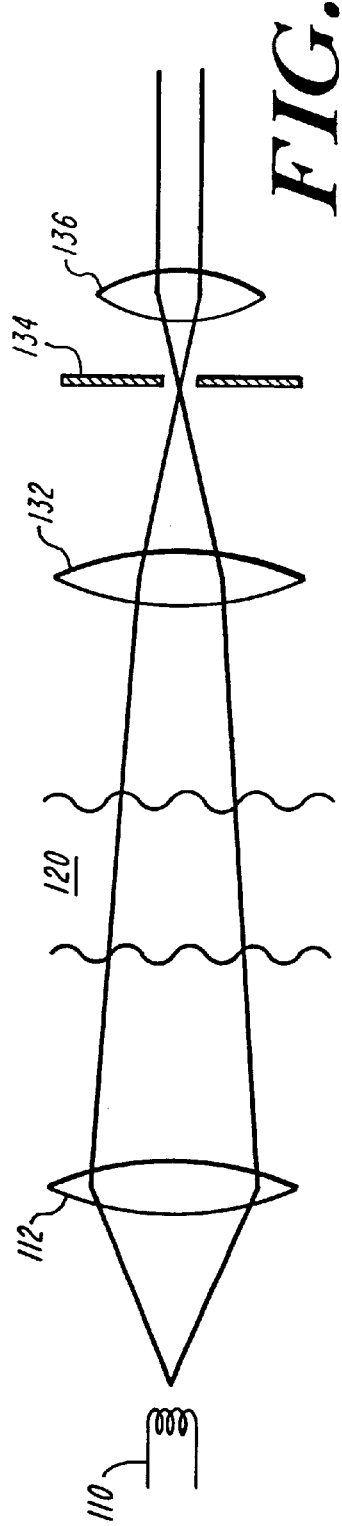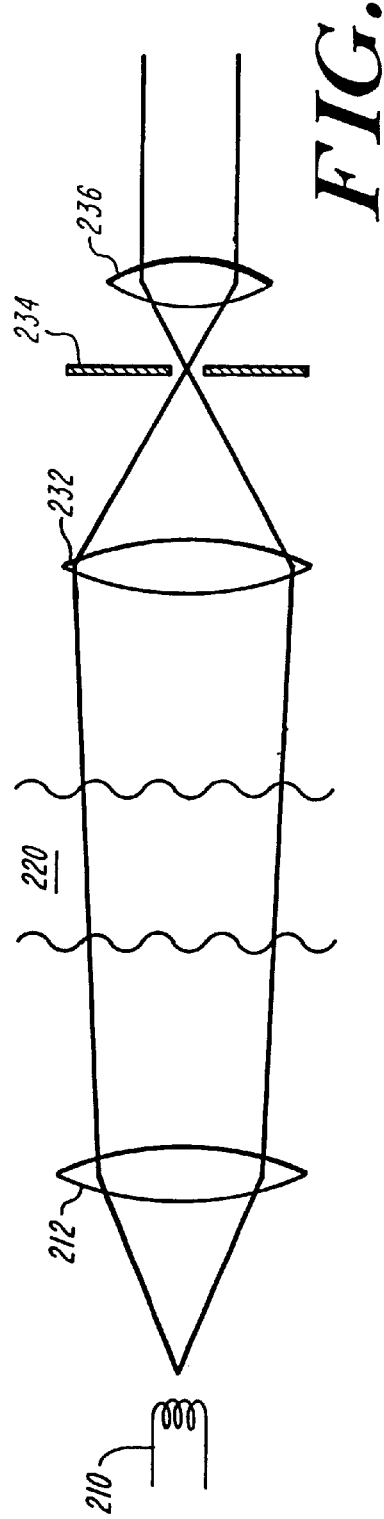

METHODS OF MINIMIZING SCATTERING AND IMPROVING TISSUE SAMPLING IN NON-INVASIVE TESTING AND IMAGING

REFERENCE TO RELATED APPLICATIONS

This application is a divisional application of Ser. No. 09/406,675 filed on Sep. 27, 1999 now abandoned, Pending, which is a divisional application of Ser. No. 08/937,934 filed on Sep. 25, 1997, now U.S. Pat. No. 6,064,065, which in turn is a divisional application of Ser. No. 08/479,955 filed on Jun. 7, 1995, now U.S. Pat. No. 5,672,875; which is a CIP of Ser. No. 08/333,758, Filed Nov. 3, 1994, now U.S. Pat. No. 5,818,048, which is a CIP of Ser. No. 08/182,572, filed Jan. 14, 1994, now U.S. Pat. No. 5,424,545; which is a CIP of Ser. No. 08/130,257, filed Oct. 1, 1993, now U.S. Pat. No. 5,434,412; which is a CIP of Ser. No. 07/914, 926, filed Jul. 17, 1992, now U.S. Pat. No. 5,334,287. The contents of all of the aforementioned application(s) are hereby incorporated by reference.

BACKGROUND OF THE INVENTION

The present invention relates to improvements in optical systems and their uses for the measurement of concentration and temperature in scattering media, and the related discrimination of subsurface features. More particularly, the invention provides methods and apparatus which minimize the ratio of diffusely scattered radiation to directly transmitted radiation reaching the detector(s) in optical concentration measurement and imaging apparatus. The methods and apparatus of the invention have special applicability to noninvasive testing, particularly for concentration measurements of materials such as glucose and hemoglobin in blood.

Recent literature is replete with articles describing attempts at performing non-invasive testing using optical measurements (e.g., infrared systems). Part of this expansion has been fueled by the spread of acquired immunodeficiency disease syndrome (AIDS), and the associated fear among public and health care personnel of AIDS. AIDS and other diseases such as hepatitis are born in the blood and can be spread by improper practice of invasive procedures. In addition, the diabetic population has also been anxiously awaiting non-invasive test instruments for many years. Many diabetics must test their blood glucose levels four or more time a day. The modern battery powered instruments for home use require a finger prick to obtain the sample. The extracted blood samples are placed on a chemically-treated carrier which is inserted into the instrument to obtain a glucose reading. This finger prick is painful and can be objectionable when required frequently. In addition, although the price has dropped considerably on these instruments, the cost for the disposable and the discomfort and health risk associated with having open bleeding is undesirable.

Accordingly, a number of groups have recently tried to make non-invasive instruments for testing a variety of analytes, particularly glucose. A recent trend in non-invasive testing has been to explore the use of the near infrared spectral region, primarily 700–1100 nm because this is the spectral response range of the silicon detectors typically used in the prior art. A wider wavelength range to ~1800 nm can be accessed by the addition of germanium and/or InGaAs detectors, and useful measurements can be made into the 2500 nm range with InSb or other detectors. The region below ~1400 nm is the most useful in transmission, as tissue is transparent enough there to allow high enough photon flux for accurate detection. Above 1400 nm, the strong absorption of water limits the penetration depth of tissue, so that useful measurements are typically made in reflectance geometry. Below 1100 nm, the penetration of the light is sufficient that the signal modulation during the arterial pulse can be measured comfortably in both transmission and reflectance geometries. Above 1400 nm, such pulsatile measurements are extremely difficult in transmission due to low intensity, and similarly difficult in reflectance because the light does not penetrate deeply enough to sample the pulsatile capillary beds.

Most of the non-invasive testing work has been carried out using classic spectrophotometric methods, such as a set of narrow wavelengths sources, or scanning spectrophotometers which scan wavelength by wavelength across a broad spectrum. The data obtained from these methods are spectra which then require substantial data processing to eliminate background; accordingly, the papers are replete with data analysis techniques utilized to glean the pertinent information. Examples of this type of testing includes the work by Clarke, see U.S. Pat. No. 5,054,487; and primarily the work by Rosenthal et al., see e.g., U.S. Pat. No. 5,028,787. Although the Clarke work uses reflectance spectra and the Rosenthal work uses primarily transmission spectra, both rely on obtaining near infrared spectrophotometric data.

The major successful application of non-invasive testing is the measurement of hemoglobin oxygen saturation with pulse oximetry. The most common method compares the percentage modulation of the intensity of light traversing a body part at two wavelengths chosen so that the ratio of their respective modulations is a relatively strong function of oxygen saturation. The observed change in this ratio is relatively large because the two hemoglobin species involved have both high enough concentrations and specific absorptions that they dominate the creation of the pulsatile signal components at the wavelengths of interest. As a result, the ratio of modulations can be attributed substantially to the two hemoglobins alone, and only needs to be measured to the order of 0.1% in order to achieve clinically significant detection limits with acceptable universality of calibration.

The optical system in typical pulse oximeters have two or more LED emitters placed side-by-side on one side of a finger, and a single detector receiving the radiation on the other side of the finger. Some more recent systems have the detector on the same side of the tissue as the emitters, with baffles preventing the direct illumination of the detector by the sources. As the sources are physically small and optically displaced from each other and the detector, the light from each detector enters the tissue at slightly different locations, and therefore travel different paths through tissue to the detector.

Despite its relatively large signal levels, pulse oximetry has well-known difficulties such as the selection of an adequately vascular sampling site on each individual and variability of the results with motion of the site and breathing by the patient, as well as sensitivity to changes in blood pressure, heart rate, temperature, and tissue hydration. Disturbances such as motion and breathing artifacts typically appear as statistical outriders, i.e., as measurements which fall well off the "average" calibration curve of the instrument obtained from a group of individuals breathing controlled gas mixtures to vary their oxygen saturation.

The calibration of a pulse oximeter is subject to these same error sources; it is not uncommon to find site-to-site variations on the same individual, with results that suggest that the calibration curve even varies, for example, with the absolute magnitude of the pulsatile signal modulation. The effort to obtain a meaningful universal calibration is clearly at odds with intra- and inter-individual physiological variations.

Despite recent efforts to improve the measurement S/N by increasing source intensities and lowering detector noise, as well as increasing the number of detectors, the frequency of outriders and the universality of calibration have not improved substantially. Thus it is clear that while the light traversing the tissue is being measured more precisely, the site- and physiologically-induced variability has not been improved significantly below the 0.1% level needed for the measurement of oxygen saturation.

While these physical and physiological interferences are marginally acceptable for oxygen saturation measurements, they set a lower limit of detectivity that is too high for other clinical analytes such as glucose and cholesterol for which the combination of concentration and specific absorption requires optical measurements to be made 100–1000 times more precise than for the hemoglobins used in pulse oximetry. The hemoglobins, which in themselves are difficult to calibrate in the presence of these site- and physiologically specific limitations comprise a major background interference for the measurement of such trace constituents as glucose.

The optical systems employed for these lower concentration analytes naturally drew on the experience of pulse oximetry, and typically employ similar arrangements of a plurality of slightly displaced LED's to extend the wavelengths sampled, or which use fiber optics to carry light to and from the sources and/or spectrometers which perform the separation of the signal into the different wavelengths employed. Displacement of the sources and wide numerical apertures for the light entering and leaving the tissue enhance the likelihood that different detected wavelengths will have sampled different portions of the medium. Many of the physiological interferences to accurate measurement are mediated by differences in the mean paths traced by light of different wavelength in traversing the intervening tissue between light source[s] and detector[s]. These path variations are produced, in part, by light scattering in the tissue, which varies with the wavelength of the light and which makes photons follow a jagged overall path from scattering to scattering. The detected signals are a complicated function of both the scattering and the total absorption of all constituents along the longer total path of the light. Thus, the present optical systems used for non-invasive measurement allow and perhaps even encourage light of different wavelengths to travel different paths through the tissue, sampling lateral and axial tissue inhomogeneities differently.

This situation violates a fundamental premise of all optical non-invasive measurement methods; namely, that the light intensity which is measured in the individual detection channels can be attributed to the analyte and not to any difference in tissue sampling. Tissue inhomogeneity produces wavelength-dependent spreading of the light which ultimately reaches the detectors, and in the extreme of high scattering and large inhomogeneity, the mixture of detector signals becomes an uncontrollable and uncalibratable average response to the physiological and biochemical conditions at the sampled site.

In addition the existing non-invasive art has employed spectrophotometric methods which limit the intensity of light detected in the individual resolution elements, and which also apply the method in a way which uses the available spectral information inefficiently. These methods were conceived primarily for accurate determination of narrow band spectral structures rather than for discriminating the presence of weak broadband features in strong broadband backgrounds that characterize the non-invasive measurement problem for constituents such as glucose. The multivariate analysis mathematics required to separate the analyte signature from strongly overlapping interferent signatures also introduces an error propagation penalty that compounds the intensity limitation by increasing the impact of detector noise on the calculated measure of concentration.

Improvements that enhance the solution of problems of interference in broadband spectra, by obtaining different raw data, are described in U.S. Pat. No. 5,321,265 (the "Block '265 Patent"). This patent sets forth a different approach in non-invasive testing as compared with the prior instruments and methods. As noted, substantially all workers in the non-invasive testing field prior to the Block '265 Patent were using classic spectrophotometric instrumentation and substantial processing in an attempt to resolve the low resolution features from the background. However, the spectra of analytes such as glucose in a human body are not discrete high resolution features which spectrophotometric instruments were originally designed to measure but rather have a few low resolutions features with much of the information contained in subtle variations of the detected intensity as a function of wavelength. As such, these spectra appear more like reflectance spectra of colored objects in the visible region. The Block '265 Patent teaches the use of an analog of human color perception to obtain meaningful data by means of methods and apparatus which utilize overlapping, broadbeam detectors to mimic the spectral response characteristics of the human retinal cones, but translated into the near-infrared. This approach, which is radically different than classic spectrophotometric measurements, provides advantageous effects in determining the concentration of glucose and other similar materials in an aqueous solution and is particularly advantageous for use with scattering media such as tissue where it also provide the added advantage of higher light flux at the detectors so that the intrinsic shotnoise limitation as a percentage of the total signal intensities is reduced.

U.S. patent applications Ser. No. 08/130,257 now U.S. Pat. No. 5,434,412; Ser. No. 08/182,572 now U.S. Pat. No. 5,424,545 and Ser. No. 08/333,758 now U.S. Pat. No. 5,818,048, the disclosures of which are incorporated herein by reference, all disclose improvements in the basic techniques and apparatus described in the Block '265 Patent. These improvements include the concepts of congruent illumination and detection of light emerging from the sampled tissue site, pulsatile processing, modulation of illumination sources as a means of eliminating unwanted radiation, the use of non-overlapping broad beam radiation as well as overlapping radiation, and a number of variations thereon. These applications make it clear, in part, that a variety of techniques are useful (and in some instances may be necessary) to deal with the problems encountered in non-invasive measurement of analyte concentration in tissue or other scattering media. Many of these problems arise from the fact that scattering media exhibit higher effective path lengths than their physical dimensions because of scattering by the samples themselves. In fact, the samples, such as human tissue, act as if they are formed of a plurality of scattering sites or centers in the sample. Techniques such as the congruent illumination and congruent detection described in these patent applications equalize the acceptance angles and distances traveled by light of different wavelengths outside the scattering media. Technically, this is achieved by locating all the illumination sources and/or detectors so that the path lengths and angles between the media and the detector(s)/source(s) are equal, so that the detectors or radiation sources act as if they were optically superimposed.

However, the desired congruency of detected light is degraded within the observed media because the multiple scatterings of light spread the light beam to adjacent regions in a way which is strongly wavelength dependent. If the scattering media is inhomogeneous, the result of this spreading is to mix light from these adjacent structures in relative amounts which are dependent on wavelength. One object of the present invention is to reduce this disturbing effect by refining the launch and detection optics to limit their angular acceptance ranges.

It has long been known that a certain portion of the illuminating radiation survives transit across a turbid sample without being either scattered or absorbed, while a much larger portion is scattered in all directions. The more scattering a particular photon undergoes the longer the integrated path it follows, and the longer the time that elapses before it emerges from of the sample. Some groups have attempted to reduce the deleterious effects of scattering by using pulsed sources and time gating the detection so as to view the sample only in light which has undergone few scatterings. What is measured is a "snapshot" of the sample in light starting at the time of flight for an unscattered beam, and extending long enough in time to obtain sufficient signal for the desired analysis without including much scattered radiation. When the time gate is short, "ballistic" or "snake-like" photons which have undergone no or few scatterings along their path are selected, and shadowgram images similar to those commonly obtained with x-ray's can be obtained.

This approach, however, requires complicated apparatus, and in addition to the intensity limitation from the short time-gate after each pulse of the light source, adds a further limitation on the number of detected photons because the duty-cycle of the pulsed source is low compared to the continuous source of the present invention. Other research groups such as Wist et al., IEEE Transactions on Medical Imaging, 12 (4) 751–757 (1993), have demonstrated that shadowgram-type images can be obtained by severely restricting the angular acceptance range of detected photons about the forward direction, essentially demonstrating that doing so limits the detection to "ballistic" or "snakelike" photons. The Wist et al. apparatus generates a geometrically narrow beam which is raster-scanned across the sample, at a first wavelength, and then generates new images at changed wavelengths. The work of this group, however, also demonstrates a severe limitation on the total flux of transmitted photons which make it inapplicable to the detection of trace constituents in scattering media.

Other workers such as Schmitt et. al., SPIE 1641, 150–161, (1992), have demonstrated advantages for using collimated input and output light on in vitro phantoms that simulate some of the light scattering properties of turbid media, but the transmitted intensity limitation of their system when it was applied to real in vivo measurements made it necessary to change the system design away from this collimated approach. One difficulty appears to be that their in vitro system was designed to "approximate the plane-parallel conditions under which [the theoretical] photon diffusion model was derived," rather than addressing the characteristics of the in vivo sample. Schmitt's collimated system was designed to approximate a "collimated beam of infinite extent" by establishing a finite incident beam of light traversing tissues and confining the collimated detection to a small central region on the exit side, apparently in order to eliminate unwanted edge effects. In addition, the narrow-band sources and detector used limited the transmitted intensity.

The failure of Schmitt's design was that insufficient photon flux was available at the detector, so that this system was abandoned for his in vivo work. Instead, Schmitt's in vivo apparatus employed a fiber optic that launched light into the tissue at its large (~50 degree) numerical aperture, and an integrating detector on the opposite side of the tissue receiving light through almost the whole hemisphere. Even then, as noted in his article, the system had inadequate light intensity for the measurement he was attempting. His work thus vividly illustrates the light transmission limitations of real tissue that characterizes the prior art.

Thus, it is a specific object of the present invention to balance the light collection efficiency and spatial resolution of the optical sampling system viewing scattering media to simultaneously achieve high detected light intensity and equality of response, as a function of wavelength, to inhomogeneous inclusions within the media This is accomplished by selecting optical configurations of sources, detectors, and intervening optical elements to minimize the effect of tissue inhomogeneities on the relative changes in signal strengths in each of the different detectors due to the presence of analyte.

It is a further object of the invention to achieve this balance in a way which improves the repeatability of the measurements from site-to-site on a given individual in the presence of disturbances such as motion, breathing, hydration, and the like, with the ultimate objective to achieve universal calibratability of the measurement across subject in the presence of such disturbances.

A related object of the invention is to provide a method of non-invasive concentration measurement in a scattering media which increases the ratio of direct collimated radiation to diffusely scattered radiation reaching the detector, while maintained high integrated light intensity at the detectors.

Another object in the invention is provide an apparatus for non-invasive concentration measurements which maximizes the ratio of direct collimated radiation to diffusely scattered radiation while maintaining high integrated light intensity.

A further object of the invention is to facilitate the use of tighter collimation by increasing the number of photons received in the individual detector resolution elements through broadening their wavelength acceptance range.

A similar objective of the invention is to facilitate the use of tighter collimation by increasing the number of photons received by individual detector resolution elements through increasing their surface area while maintaining their congruency.

Yet another object of the invention is to further facilitate the use of tighter collimation by the use of overlapping broadband detector resolution elements in an analog of human color perception to combine increased photon flux with more efficient separation of similar broad analyte and interferent spectral features.

Consequently, it is a specific object of this invention to select optical configurations of sources, detectors, and intervening optical elements to minimize the effect of tissue inhomogeneities on the relative changes in signal strengths in each of the different detectors due to the presence of analyte.

It is a still further object of this invention to adjust the optical interface to take maximum advantage of the natural spreading characteristics of the light distribution patterns in tissue in maximizing the S/N of the determination.

These and other objects which features the invention will be apparent from the detailed description and the drawing.

SUMMARY OF THE INVENTION

The present invention features methods and apparatus for measuring concentration in a sample which contains a plurality of radiation scattering sites, and for measuring the distribution of concentration and/or temperature within a sample when employed with imaging detectors. The methods and apparatus can also be utilized for discrimination of subsurface features through shadowgram generation. This procedure is also useful for detection of temperature inhomogenieties. The methods and apparatus of the invention employ means for restricting the solid angle of illumination and/or collection, e.g., by collimation of the radiation to minimize the amount of scattered radiation collected, employ polarization of the illuminating radiation to differentiate scattered from unscattered radiation, or a combination of the two. The methods and apparatus of the invention provide more reproducible measurements on scattering media and are particularly well suited to non-invasive testing of tissue for materials such as glucose and drugs of abuse.

More particularly, the present invention provides a method of measuring the concentration in a sample of a selected substance which absorbs radiation in a particular region of the spectrum. The sample containing the substance of interest also contains a plurality of sites which scatter radiation in the same particular region of the spectrum. The method has the steps of illuminating the sample with broad geometric area illumination within a particular region of the spectrum (preferably using broad spectrum radiation) where the substance of interest has absorption, with the illumination and detection solid angles restricted, and with both said solid angles extending over a geometrically wide surface cross-section. The term "broad spectrum illumination" as used herein means and implies that the wavelength of the illumination covers a substantial portion of the region of the spectrum in which there is absorption by the selected substance. Normally, the illumination is greater than 50 nm wide, and if the substance of interest has absorbance at several wavelengths in the particular region, it preferably is wide enough to cover all of the absorption bands.

After leaving the sample, radiation which is transmitted or reflected from the sample is collected with a detector, the detector being selected and located such that the each resolution element of the detector collects radiation only from a limited solid angle extending over a relatively wide area of the viewed surface. The restricted solid angle illumination also extends over a relatively wide area of the illuminated surface. The term "wide" as used herein implies a beam width that is comparable or larger in size than the thickness of the tissue being viewed. The term "comparable" means and implies that the width of the beam or viewing area is at least half the thickness of the sample or tissue. That thickness is itself preferably restricted to be not much deeper than several "natural" 1/e penetration lengths, the depth over which the diffuse radiation photon density falls to a few percent of its maximum value near the entrance surface of the medium. For typical tissues viewed in the 700–1400 nm wavelength range, these preferred thicknesses are of the order of a few mm, and the surface areas through which the light enters and exits are both in the 5–10 mm range.

The terms "restricted solid angle" and "limited solid angle" as used herein imply that the type of detector or illuminating radiation, which may include some form of filtering and/beam focusing apparatus, limits the angle over which the illumination or detection occurs. Preferably, the illumination and or detection is restricted to a solid angle of about 10° or less from the central illumination beam axis. This configuration maximizes-the ratio of directly transmitted radiation to scattered radiation collected by the detector from the sample. Preferably, the restricted solid angle of illumination is achieved by collimating the radiation from the radiation source prior to illuminating the sample, most preferably with collimating optics such as described herein. Alternatively, a laser or another source which provides restricted divergence illumination may be used without the necessity of some type of collimating optics.

Similarly, the preferred detector limits the solid angle of the detected radiation transmitted from said sample by excluding uncollimated radiation prior to collection by the detector. Again, collimating optics, such as a combination of lenses and/or apertures, can be used. Alternative collimating optics known in the art, such as a channel plate or a honeycomb collimator, can be used as well. Some of the benefits of the method may be achieved by comparing the results for two or more narrow angular acceptance ranges at different angles relative to the central axis of the illumination beam. In fact, using a second, off axis detector can assist in identifying the contribution of diffuse radiation and assist in correction for motion and other artifacts. In another embodiment, it is advantageous to have congruent detectors viewing the scattering media on the same side as the illumination, in what is commonly referred to as a reflectance or transflectance measurement geometry. Certain tissue sites, such as the forehead, may be particularly advantageous in this geometry because the vascular tissue between the skin and the bone has a thickness comparable to the "natural" penetration depths, and the bone serves as a relatively inert backing that isolates the overlying tissue from other analyte containing deeper tissue.

In addition to the strictly collimated beam, a combination of selected slightly converging or diverging beams generated by a combination of lenses and/or apertures can be used in the present invention. In one aspect of the invention, a first converging lens is selected and located on the illumination side of the sample such that its focal point for the illuminating radiation is located on the detection side of the sample and the first converging lens. In this embodiment, limiting the solid angle viewed by the detectors may be achieved by means of a second converging lens between the sample and the detector which has a limiting aperture mask at its focal distance so that the size of a central hole in that mask defines the angular acceptance range. This same type of second converging lens is used on the illumination side. After passing through this aperture, the light beam is then expanded once again and passed through the congruent beamsplitter arrangement described in U.S. patent applications Ser. No. 08/130,257 now U.S. Pat. No. 5,434,412 and Ser. No. 08/182/,572 now U.S. Pat. No. 5,424,554 in the following examples. If this configuration is used to collect light in other than the forward direction, the entire lens/aperture/detector assembly would be rotated about an axis centered preferably beneath the surface of the viewed sample.

The optics of the system and methods described herein are such that they eliminate much of the scattered radiation reaching the detector, specifically all the scattered radiation outside the limited solid angle viewed by the detector, while allowing the use of geometrically wide radiation beams. This enhances the ratio of directly transmitted to diffuse radiation which reaches the detector. This is particularly advantageous with a heavily scattering media, e.g., the sample is a portion of an mammalian body, such as a human body. If a human body is used as a sample, preferably a thin region of tissue is selected so as to minimize person-to-person variation in tissue thickness. Once again the preferred thickness would lie in the range of a few (2–10) mm, comparable to the distances over which the internal light density falls to a few percent of its maximum value. Thinner tissues can be used provided that they are sufficiently vascular to provide good pulsatile signals. One possible area for use is a finger web which can be clamped to provide a substantially standardized tissue bed thickness. Another alternative is the eyelid. Thinner tissues such as these can also be backed by reflective surfaces to achieve a "double-pass" effect, or with an absorbing backing that also isolates the tissue from underlying structures.

The geometrical width of the illumination and detection areas on both sides of the sample are designed to be wide enough to average over multiple internal structures such as capillary beds. This reduces sensitivity of the results to the exact positioning of the optical system at the chosen site. This approach achieves significantly higher integrated light intensity at the detectors, while avoiding edge effects at the extremes of the illumination beam. Thus, the large geometric beam area facilitates passage of a large number of photons, and the solid angle restrictions limit differences in the lateral spreading of the light within the tissue at different wavelengths. This geometry produces relatively higher detected light intensity with more consistent sampling across tissue inhomogeneities as a function of wavelength than does previously described apparatus and methods. The intensity is high enough that the fundamental shot-noise detection limit falls below the precision needed for the trace analytes of interest, and the improved sampling reduces the non-linearities imposed on the measurement calibration by scattering.

The preferred working range for the method and apparatus invention is from about 700 to about 2500 nm. This region covers the absorbance of some of the most preferred substances, including glucose and its identifying substances, hemoglobin, deoxyhemoglobin and various drugs of abuse. The method can be used to determine the hemocrit or to derive the oxygen saturation level in the blood. This method and apparatus can be made sufficiently rapid to measure arterial pulse data, thereby eliminating another source of potential error. The present improvements can also be utilized with modulated sources, which are particularly helpful in eliminating radiation generated from sources other than what is transmitted by the sample.

In an other embodiment of the invention, polarized light is used as the illuminating radiation. The detector which collects the radiation includes an analyzer or filter for transmitting polarized light before, or as part of, the detector, while excluding depolarized light transmitted from the sample. Since scattering of polarized radiation by the scattering sites in the sample will depolarize the scattered radiation, the use of the polarizer in conjunction with the detector will maximize the ratio of polarized radiation to depolarized radiation collected by the detector. The preferred polarization system has the restricted solid angles of illumination and limited solid angle of detection previously described. The reason for this is, in part, that using this technique not only eliminates scattered radiation but also eliminate radiation from other non-polarized background light sources and provides the highest ratio of desired to undesired radiation while providing sufficient signal.

If the restricted solid angle geometry is utilized for imaging, an array of detector units forming the detector, e.g., a CCD array, can be used. This array, and/or illumination source, can be scanned across the sample using any standard mechanical stage or raster scanner, to generate a series of shadowgrams which can be combined to form a larger shadowgram showing tissue inhomogeneities. Temperature changes across the tissue can also show up as an inhomogeneity.

As noted, the present invention also provides a device or apparatus for carrying out the method of the invention. All the aspects previously described with respect to the methods can be utilized in the apparatus.

The invention is further illustrated by the detailed description of the invention and the drawing.

BRIEF DESCRIPTION OF THE DRAWING

FIG. 4 shows two variations on optical systems for the invention, with FIG. 4A having a slightly converging illumination beam while FIG. 4B has a slightly diverging illumination beam, and the detector on each showing collimating optics;

DETAILED DESCRIPTION OF THE INVENTION

Figure 1:
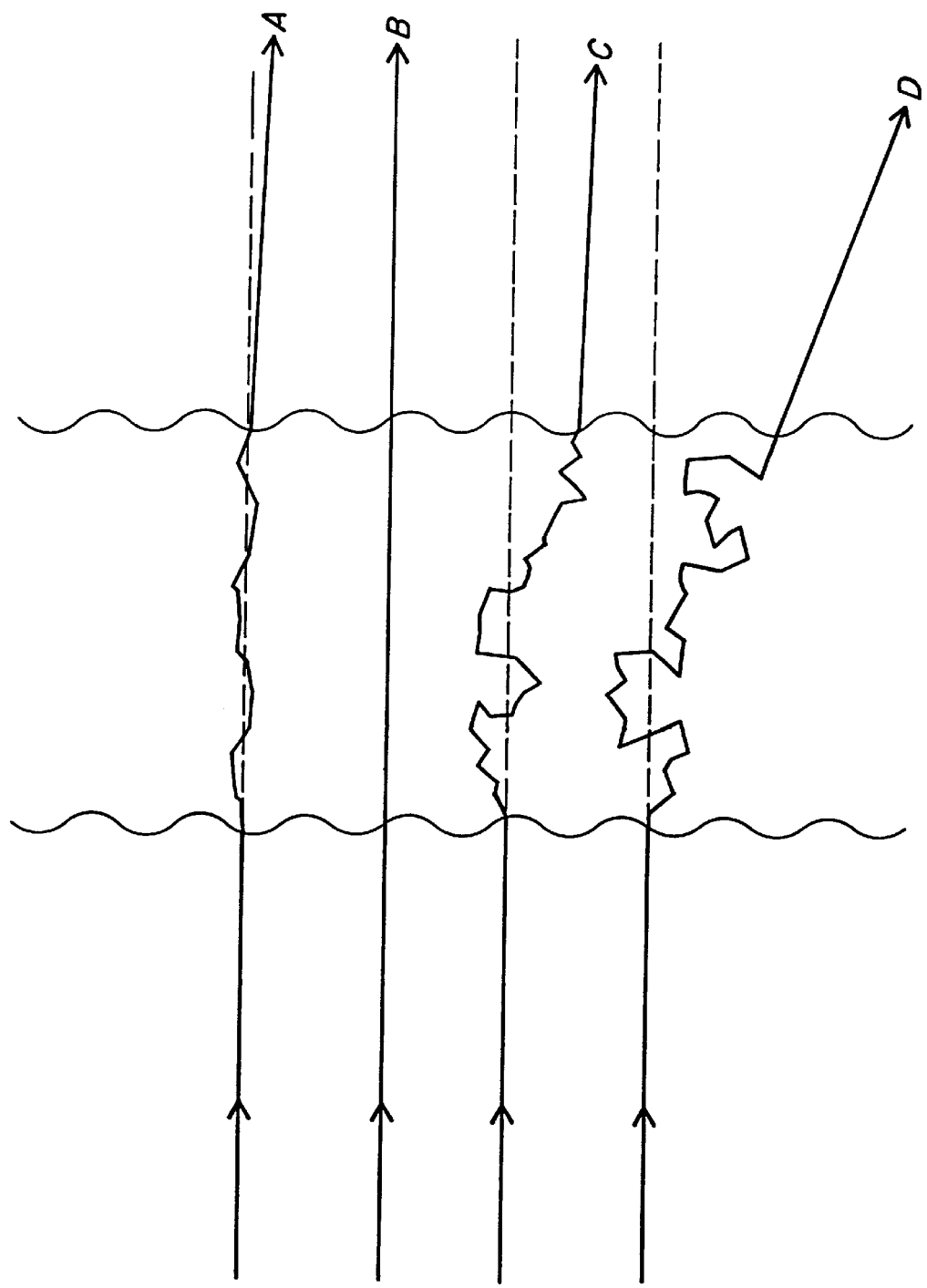
FIG. 1 shows several possible characteristics of beams which pass through a tissue sample.

The present invention is directed, in part, to methods of improving consistency of measurement and, therefore, calibration of samples which have scattering properties. The methods and apparatus of the invention are particularly well suited to non-invasive testing of human tissue. The invention is based, to a large extent, on the recognition that if sufficient signal is generated in a non-invasive test system, limiting the solid angle such that much of the scattered radiation would be outside the solid angle of detection would minimize changes in the effective pathlength caused by unequal scattering in the sample.

One of the advantages described in the Block '265 Patent, as well as the other above-cited United States patent applications, is that the use of broad spectrum illumination and detection provides greater signal intensity than in a conventional spectrophotometric systems. High detected intensity is vital for the detection of the specific absorption of trace analytes, because the changes they make in the detected signals are very small. The signal changes produced by clinical concentrations of glucose, for example, as so small that they are difficult to separate in aqueous solution from changes due to the displacement of water and slight alterations in solution temperature. As a result, there are no reliable publications of the specific absorption spectrum of glucose in solution in the near infrared. Nevertheless, the scale of glucose absorption can be approximated on the assumption that the hydroxyl groups of glucose create an average band whose size and shape are similar to the corresponding band of pure water, but whose location is shifted by interactions with adjacent groups on the molecule to have a peak slightly above 1010 nm. At 5.5 mmol/L (100 mg/dL), these glucose-bound hydroxyl groups are about 2000 times less concentrated than those of bulk water. By scaling from the 0.2 OD absorption band of pure water at 960 nm, the shifted band-peak from glucose at 5.5 mmol/L concentration would have a magnitude of about $10^{-4}$ OD at 1 cm path, which would create a transmission change of $2.3 \times 10^{-4}$. This result agrees with the general level observed for this shifted OH band in higher concentration measurements reported by Koashi in U.S. Pat. No. 4,883,953 for the chemically similar saccharose.

To be clinically useful, this glucose concentration should be measured with a precision roughly 20 times smaller, which translates to a measurement resolution or precision at the one part in 100,000 level in the case when the tissue viewed has an effective pathlength of 1 cm. If pulsatile measurement is employed, the time-varying component s of the signals, which typically comprise 2–10 percent of the total signal, must also be measured to sufficient precision. Here, however, the effective pathlength generating the observed pulsations is much shorter than 1 cm. For example, in the 950 nm range, the dominant absorber in the blood is oxyhemoglobin, with total absorbance of about 3 OD for a midrange hemoglobin concentration. Such an absorbing solution creates 10 percent change in transmission at a pathlength of only 1/60th cm. As a result, the pulsatile measurement of specific glucose absorption requires precision better than one partper-million.

This is significantly below the repeatability achievable with the present stateof-the-art in pulse oximetry The photodetector shot noise limit alone require that there be more than $10^{12}$ photoelectrons detected in the integration time of the measurement to reach the part-per-million resolution range. Allowing for the fact that only a portion of each arterial pulse is useful, the shot noise limit translates to a requirement for intensity levels at the photodetectors which lie in the 10–100 microwatt range, after passage through the tissue. With thick tissues and/or inefficient use of intensity, this requirement in turn can lead to a need for 10–100 milliwatts, o r even watts, of radiation launched into the tissue. The intensity which can be used has a practical upper limit set, at least, by the levels which become uncomfortable for the test subject due to heating by the absorbed radiation.

Sensitivity at the part-per-million range also enables the measurement of the temperature of subsurface features with milli-degree°C. sensitivity, or lower. This follows from the fact that the 960 nm water band changes its distribution with wavelength when the temperature varies, thereby allowing the temperature to be visualized by imaging detectors just as if it were another absorbing constituent. Our measurements with four 70 nm wide overlapping filters positioned near the 960 nm absorption band of water have shown that a 1° C. temperature deviation produces signal deviations that are on the same approximate scale as those due to the intrinsic absorption bands of glucose at a concentration of about 110 mmol/L (2000 mg/dL), but with a different distribution between the four detector signals. When the signals from imaging detectors are analyzed to display the mean subsurface temperature along the collimated path through the tissue, the resultant "shadowgram" images allow the localization, for example, of regions of high metabolism, such as tumors.

It is known that light transmitted through tissue or other scattering media can pass through in a variety of ways. FIG. 1 shows a sampling of these modes of transmission, in the form of a series of ray traces. More particularly, ray trace A on FIG. 1 shows a "snake like" ray which only has minor, glancing scattering collisions through the tissue. This type of scattering comprises a forward-scattered ray. Ray trace B shows a "ballistic" ray which travels directly through the tissue without being scattered or absorbed; that is, it passes directly through the tissue, being transmitted forward as if there were no scattering centers in the sample. Differentiation between "snakelike" and "ballistic" rays is difficult, and those who attempted time gating normally include both types of rays in their collected data Ray trace C on FIG. 1 is a multiply scattered ray that emerges within the selected angular distribution range accepted by the detector. This type of ray will be deemed a forward scattered ray by the apparatus and it will be measured or included as part of the presumed "unscattered" radiation. Ray trace D is a multiply scattered ray which scatters outside the selected angular detection region viewed by the detector. For convenience, this multiply scattered ray is shown as being only slightly outside the solid angle viewed by the detector but actually multiply scattered rays outside the solid angle viewed by the detector would constitute the majority of the radiation hitting the sample.

In the visible and near infrared, the relative abundance of these various ray types is a very strong function of the thickness of the tissue, the magnitudes of the scattering and absorption cross sections for the selected tissue sites, and on the socalled single scattering phase function (sometimes called the angular scattering distribution). The cross sections and phase functions vary strongly between tissue types, and within given tissues depend strongly on the state of hydration and patient-dependent mixture of physiological substructures.

There has been much attention paid recently in the literature on methods to measure, interpret, and extrapolate from these fundamental measurements to obtain single scattering parameters and bulk absorption scattering coefficients for the media. The theoretical problem, however, is complex and does not lead to closed-form solutions unless severely restrictive assumptions are made. The situation is further complicated by the fact that the coefficients themselves are strongly tied to the underlying theoretical model, so that much care must be taken even to compare coefficients obtained by different workers to be sure that they are defined and measured in the same way. In general, the theoretical models have not yet been able to deal well with nonhomogeneous tissue, and provide only general guidance on the scale and functional dependencies to be expected in real measurements.

As a result of the complexity of theoretical models, the Monte Carlo calculational method is often employed. Here, the paths of many photons such as those indicated in FIG. 1 are followed through their transit across the scattering medium. The frequency of interaction and the angle of each scattering are selected randomly by the computer so as to be consistent, on the average of all interactions, with the assumed fundamental cross sections and phase functions which form the input data for the calculation. While this method readily accommodates nonhomogeneous media, it is very ponderous for the solution of the inverse scattering problem in which the cross sections and phase functions are determined from the observed experimental measurements. Here again, the results provide only general guidance as to how the measurements will vary with experimentally controllable parameters.

There is agreement in the literature, however, that in the limit of small angular acceptance for a parallel initial beam incident on a semi-infinite plane slab of tissue or other scattering media, the transmission of light in the forward direction follows the classic form of Beer's law:

$$T = e^{-(\mu_s + \mu_a)x} \quad [1]$$

where $\mu_s$ designates the coefficient of scattering, $\mu_a$ is the total absorption coefficient made up of the sum $\mu_{a\ 1} = \mu_{a1} + \mu_{a2} + \mu_{a3} + \ldots$ of the absorption coefficients of the individual constituents present in the scattering media, and x is the thickness of the slab. While $\mu_a$ is relatively independent of the experimental setup, $\mu_s$ depends strongly on how small a solid angle the detector subtends in the forward direction (i.e., the smaller the angle, the easier it is for a scattering event to remove a photon from the detected beam, and the larger $\mu_s$ becomes). When the detector solid angle and/or the thickness are small enough that equation [1] is followed, scattering affects the transmission with the identical functional dependence as any of the absorbing constituents. Further, the contributions of layered media can be readily calculated by dividing x into a sum over the individual layer thicknesses. Note that with this exponential dependence the effect of a strongly absorbing layer on the transmission is independent of the layer depth within the composite medium; such a layer produces the same percentage change in the transmission wherever it lies along the optical path.

There are many different theoretical models in use to describe the transport of light across scattering media, most of which are based on the available closed form solutions to a diffusion equation. To couple these available solutions to the real scattering problems, these models typically assume a point source of light, completely diffuse illumination, or a rapid transition from a parallel input beam of light to a highly diffused beam. Once such diffuse illumination is established, it typically propagates through the tissue with a relatively stable angular distribution that rapidly approaches an isotropic one whose magnitude decays with distance following a functional form similar to:

$$T = e^{-\sqrt{3\mu'_a(\mu'_s + \mu'_a)}x} \quad [2]$$

Here the prime (') indicates that the coefficients in equations [2] are not the same as in equation [1]. The magnitudes of the coefficients are in fact quite model dependent, while the functional form is generally model invariant.

Equation [2] is only applicable for one dimensional models in which the angular distribution of the light reaching the detector is ignored. Theoretical models with three dimensional geometries produce equations similar to equation [2], with T replaced by the photon density, x replaced by the radius r from the coordinate origin, and with additional factors of $1/r^2$ present to account for the loss in absolute photon density as the approximately isotropic beam spreads radially.

A similar form also develops in the well-known Kubelka-Munk scattering theory, with the characteristic exponential decay constant $3\mu_a'(\mu_s' + \mu_a')$ of equation [2] replaced in more complicated combinations of exponentials by K(2S+K), where K and S represent bulk absorption and scattering coefficients of the media defined specifically under the constraint of perfectly diffused incident and transmitted (or reflected) light distributions. The slight difference in the functional form of these exponential terms results from the details of the differential equation whose closed form solutions are used to approximate reality. Thus, in the Kubelka-Munk formulation a one dimensional differential equation is assumed with cross-coupling constants K and S between two isotropically distributed light beams progressing in the forward and backward directions. All the three dimensional information is carried in the assumption of well-maintained-isotropy. Despite their differential genesis, it is clear that suitable renormalization can carry the K-S form into the $\mu_a' - \mu_s'$ form.

Over most of the 700–1400 nm range, $\mu_a'$ is much smaller than $\mu_s'$ (see Wilson et al., IEEE J Quant Elec 1990; 26, 2186–99 for a review), and the second term under the square root in equation [2] is often dropped in the theoretical analyses. Above 1400 nm, $\mu_a'$ undergoes a tenfold increase because of increased absorption by water. The exponent of the transmission in equation [1] is often referred to as the "transport mean free path (mfp)," with $\mu_s'$ also including a correction for the average cosine of the scattering phase function. For typical tissues, the mfp usually lies in the range of 0.05–0.2 mm. Similarly the exponent of the transmission in equation [2] is called the penetration depth, i.e., the distance at which the diffuse radiation levels fall to 1/e. For typical combinations of coefficients and phase functions, this is 10 to 20 times larger than the mfp, and ranges up to a few mm.

Figure 6:
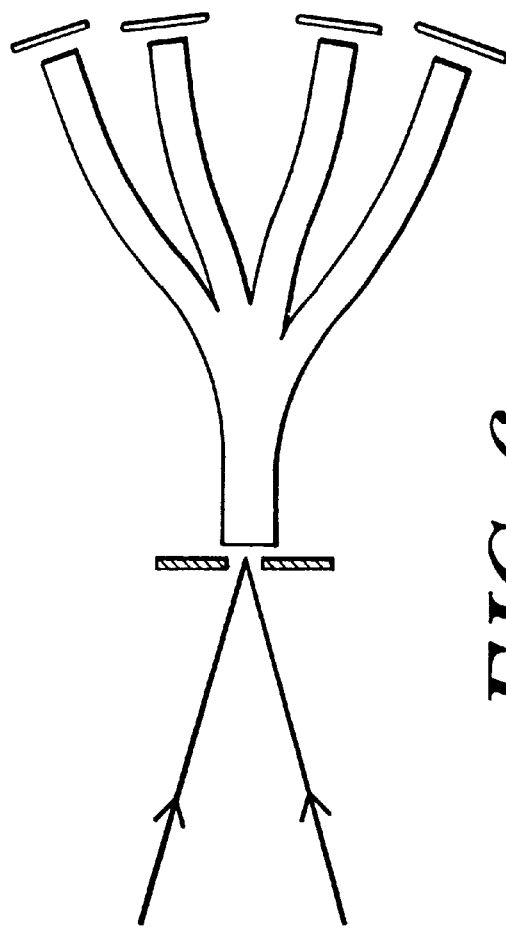
FIG. 6 shows a system wherein a bifurcated optical bundle may be substituted for the congruent sampling apparatus shown in FIG. 2.

Monte Carlo models, such as those of Flock et al., IEEE Trans Biomed Eng 1989; 36, 1162–8, provide some guidance on the relative size of collimated and diffuse radiation beams. FIG. 6 in the Flock et al. paper is a polar plot of intensities for "ten bins of equal solid angle." While the most forward bin shown in this figure appears to have a smaller solid angle than the others, the figure does indicate that the collimated and diffusely transmitted photons will have roughly equal intensity at depths of about 20 transport mean free paths, comparable to the natural penetration depth of the diffuse radiation. The distance for such equivalence is clearly a strong function of the angles and fundamental coefficients and those of the site.

The important result is that the scattering and absorption effects are mixed together, so that neither acts alone; an increase in one of them with wavelength or sampling site enhances the impact of the other on the transmission. When scattering dominates over absorption the dependence of the exponent on $\mu_a$ in equation [2] changes from a linear one similar to equation [1] to a square root dependence, and the usual logarithmic transformation of Beer's law that linearizes equation [1] can no longer linearize equation [2]. It is worth noting that equation [2] does not converge smoothly to equation [1] as the scattering coefficient goes to zero because of the extra factor of 3 in the equation [2] exponent, again highlighting the model dependent normalization differences.

The difficulties inherent in the calibration of diffuse transmission are illustrated by the work of Cope et al., SPIE 1431, 251–62 (1991), who coalesce the square root and $3\mu_s'$ factors in the exponent of equation [2] into a new variable they call the differential pathlength factor ("DPF"). The DPF is a locally linear approximation to the slope of the square root dependence after logarithmic transformation which must be calibrated separately at each wavelength of interest with the implicit assumption that the bulk coefficients $\mu_a'$ and $\mu_s'$ and the thickness x' will remain constant between the calibration and analysis samples. Cope et al. found that use of such a wavelength dependent DPF with these assumptions "significantly improved the residuals generated by multilinear regression analysis." At the same time, they also note that the calibration of the DPF is impractical in vivo, where $\mu_a'$ can not be varied independently, and instead propose an additional measurement of the mean time of flight of detected photons as a measure of the DPF. Their calibration method is clearly highly complex even for this case in which the analyte itself contributes roughly 1/10 of the total bulk absorption coefficient $\mu_a'$. This is 1,000–10,000 time higher than the equivalent relative contribution of glucose to the total absorption in the present invention.

As noted in the U.S. patent application Ser. No. 08/333,758, the small size of the analyte absorption allows a convenient alternative calibration method in which the effect of the analyte is to create small linear perturbations of the signal intensities from a set of reference intensities which are defined by the absorption of major constituents, such as the hemoglobins, and the thickness and scattering characteristics of the sampled site. These reference intensities are themselves highly non-linear, comprising a mixture of the functional dependencies of equations [1] and [2]. The preferred methods described in the Block '265 Patent and the related application take advantage of the broad and shallow wavelength variations of the major absorbers and the scattering characteristics of the tissue to facilitate the accurate determination of the reference intensities, and do so dynamically on each individual measurement so as to adjust automatically for the inevitable physiological changes in the selected sites from day-to-day. The use of restricted solid angle, particularly in the form of collimation carries the functional behavior closer to that of equation [1] as the effects of scattering, absorption, and thickness become decoupled so that the estimation of the reference intensities become more reliable and more easily calibrated. This trend applies across the whole spectrum of calibration methodology disclosed in the related patent and applications, including the simultaneous intercomparison of measurements on multiple sites and/or with multiple detector configurations with different wavelength responses.

Most importantly, neither the theoretical models outlined above nor the experimental measurement systems employed using classical methods deal well with the inhomogeneities in tissue and other layered scattering media. Closed-form solutions only appear for extremely limited assumptions of the mutual variation of $\mu_a'$ and $\mu_s'$ with depth into the scattering medium. The Monte Carlo approach can handle tissue inhomogeneities somewhat better, but also require input values for the coefficients and the angular distributions of single scattering events that are very difficult to obtain reliably. Even the early experimental work of Kubelka, J Opt Soc America (1954) 44, 330–5, demonstrated that in diffuse light, the impact of an inhomogeneous layer is very strongly dependent on its depth when viewed in reflectance, and somewhat less strongly when viewed in transmission. His transmission results also showed a remarkable symmetry of the effect of a strongly absorbing layer in which it has the identical impact on the total transmission in two locations that are symmetrically offset from the midpoint of the medium.

Little theoretical work has been done as yet on the impact of lateral inhomogeneities within individual layers in the scattering medium. These are on the one hand equivalent to classical wedging errors in spectrophotometry, and on the other hand potentially more complicated because of the non-linearities inherent in the admixture of diffuse light. At the same time, the available sites for non-invasive measurement of glucose and other trace constituents can not be expected to be homogeneous at the part-per-million level within a given individual, let alone across a population of individuals.

Figure 2:
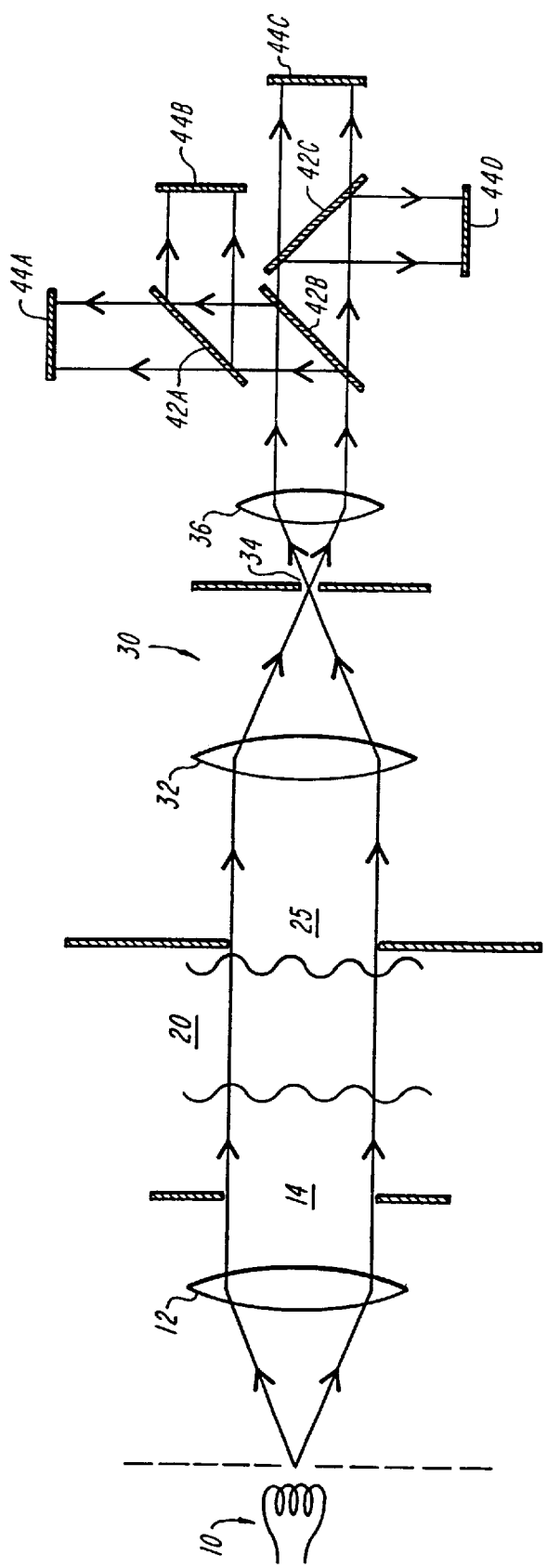
FIG. 2 shows the preferred embodiment of the invention, a device having a collimated source, collimation optics on the detector side and four detectors arranged for congruent sampling.

One preferred embodiment of the present invention, which is designed to address the simultaneous need for high detected intensity and tolerance of inhomogeneity in the sampled tissue, is shown in FIG. 2. This optical system represents an improvement over those taught in the '265 Patent and related applications, in that additional optical elements have been added to decrease the angular range of light leaving the tissue which will be accepted into the detector elements. The attendant loss of intensity at the detectors is compensated by increased size of the detectors, beamsplitters, and the geometrical area of the incident and detected light beams.

This optical system employs collimating optics for both illumination and detection, with the detector having a plurality of detector units placed such that they achieve congruent sampling. Radiation source 10 is selected so that it provides broad spectrum illumination, e.g., 700–2500 nm illumination. Radiation from radiation source 10 passed through collimating lens 12 before striking tissue 20. Optional aperture 14 is shown which helps define the collimation optics in conjunction with collimating lens 12. Tissue sample 20 may be any sample but a thin, repeatable sample such as a finger web is preferred. For this type of thin sample, the amount of scattering is minimized and it is possible to hold the web and compress it such that a standardized thickness may be achieved. The more standardized the thickness is, the more likely universal calibration (or calibration to a limited group of thicknesses) can be. If universal calibration can be achieved, the calibration can set at the factory and corrections for effective pathlength can be made in the instrument itself. If such universal calibration is not achieved, some calibration measurements may be required before meaningful data can be obtained.

Once the radiation has traversed tissue sample 20 and exits the tissue through area defining aperture 25, it passes through detector collimating optics 30 formed of converging lens 32, aperture 34 and recollimating lens 36. This type of collimating optics is conventionally used in telescopes and other devices where collimation of light is desired. The collimated beam exiting collimation optics 30, specifically recollimating lens 36, then goes through a series of beam splitters 42A, 42B and 42C and onto four detector units 44A, 44B, 44C and 44D. The beam splitters and detector units are arranged such that the entire detection unit 40 provides congruent sampling of the beam. More particularly, the beam splitters and detector units are arranged such that the pathlength and angles from recollimating lens 36 to any of detector units 44 are equal and each of detector units 44 are optically superimposable upon the other. More details of this type of congruent sampling is set forth in U.S. patent application Ser. No. 08/130,257. Although four detector units are shown, the exact number may be varied.

FIG. 2 also shows an additional testing or detector unit 50 (shown as a "black box") which is not in line with the collimation or angle restricting optics. In some circumstances, the scattered radiation may provide information in addition to or supplementing that obtained from the unscattered radiation. Additional detector unit 50, which may actually be a plurality of detector units, can be used at different positions and angles, thereby testing the scattered radiation and providing additional information. One particularly valuable embodiment uses this detector unit in reflectance or transflectance mode, that is on the same side of the tissue as the illuminating optics. This additional detection unit can be used with any of the embodiments shown herein.

The optical system of FIG. 2 preserves spatial information, in that there is a one-to-one correspondence between a location on the viewed tissue surface area and a location on the active area of each detector. With adjustment of lens-aperture-lens-detector distances, a reasonably sharp focus can be achieved, particularly as the accepted viewing solid angle shrinks towards perfect collimation. As a result, replacement of the detectors shown in FIG. 2 by imaging devices such as CCD's or other array detectors creates an imaging system that produces "shadowgrams" using "ballistic" or "snakelike" photons, with the added advantage of simultaneous congruent imaging in all pixels in the detector arrays. The simultaneity facilitates the real-time processing of the signals to form tuned images of subsurface structures in the different analytes, including temperature. Since certain tumors are known to have a different temperature than surrounding tissue, this imaging system has uses for detection of tumors and other anomalies. The illumination source and detector array can be scanned across a large tissue sample and combined to form a larger shadowgram.

Figure 3A:
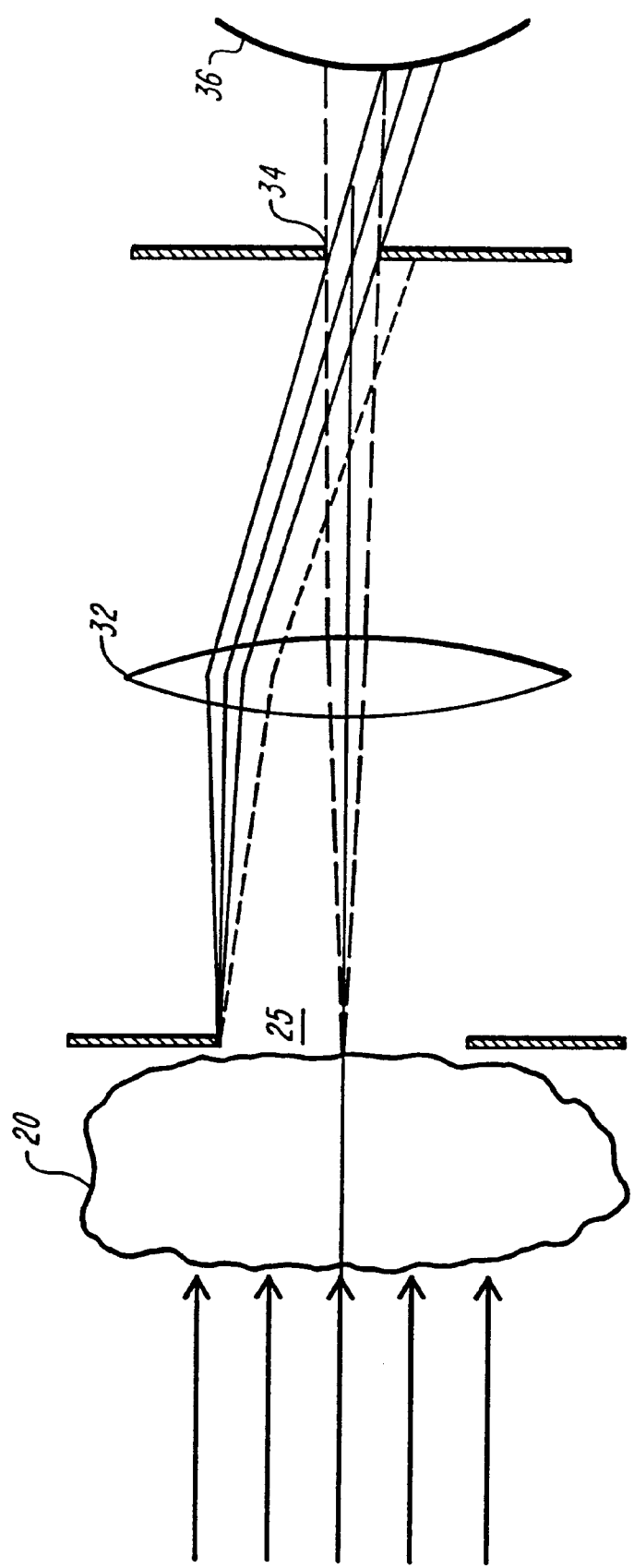
FIG. 3A expands the scale of FIG. 2 to illustrate the definition of the angular acceptance ranges by the aperture.

The essence of the present invention relative to the prior art is illustrated in the sequence of FIGS. 3A–E. FIG. 3A is an expanded scale version of FIG. 2, showing the way in which the collecting lens and angle defining aperture function to limit the acceptance cones of the light emerging from the tissue at different point on the exit area. Light emerging from the tissue at angles outside the acceptance cone from anywhere in that exit area, defined by aperture 25, strike the angle defining aperture outside its central opening. As the relative magnitudes of the forward collimated light intensity and the diffuse scattered light intensity are not know exactly from either theory or experiment, as explained above, the aperture size and the resultant angular acceptance cone must be tailored to the particular observation sites selected.

Figure 3B:
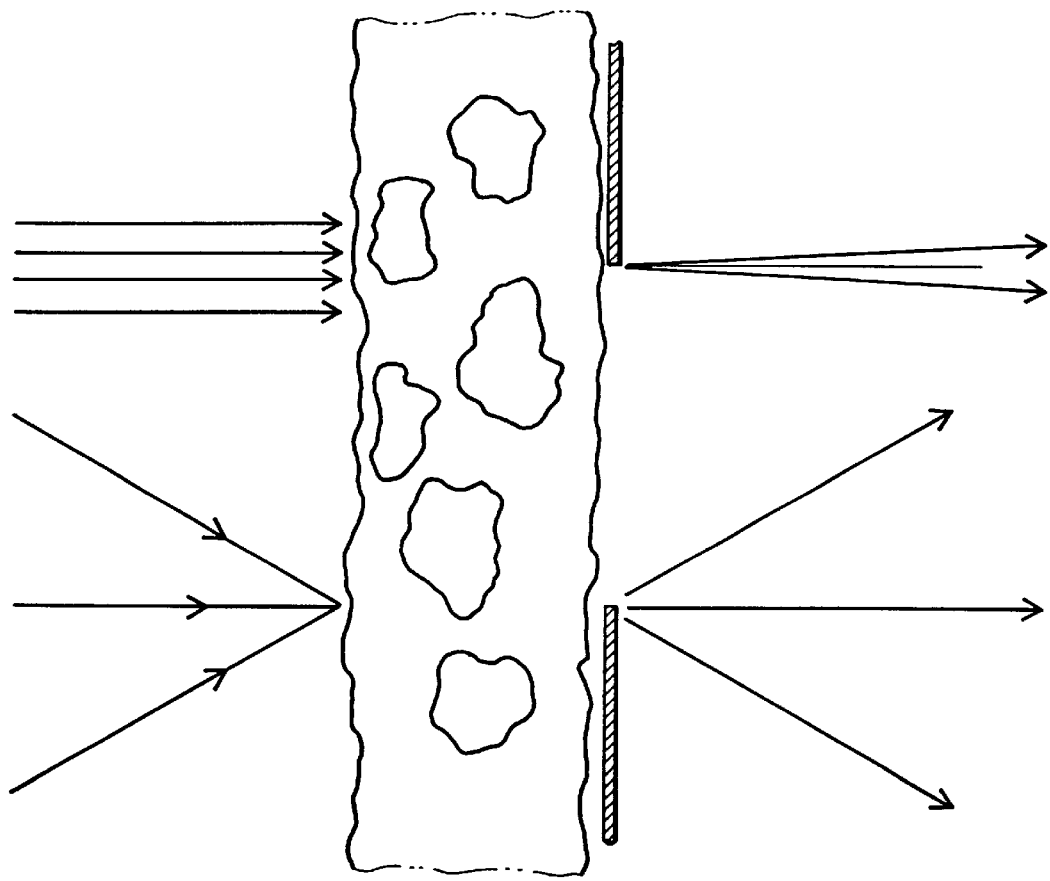
FIG. 3B further expands the scale to compare the angular divergences of the present invention with those of prior art using fiber optics.

FIG. 3B illustrates the difference between the present invention (top) and prior art (bottom) systems using fiber optics to introduce incident light to the scattering media, and then transport the transmitted light to analysis means. The angular ranges over which incident and detected light are launched or received by the optics are indicated by the arrows. These angular range for fiber optics cover their full numerical aperture, which typically comprises an ~50 degree full angle cone, while the present invention illuminates the tissue with nearly parallel light, and detects light emerging in only a small angle cone whose full angle is less than 20 degrees, and preferably less than 10 degrees. Light entering along any of the rays shown in the figure will spread sideways about that ray due to scattering, and the amount of spread will vary with the wavelength of the light. Light which has spread laterally has a much higher probability of reaching the detector in the prior art arrangement shown because the receiving fiber optic will accept light over a much higher solid angle. The arrangement shown for the present invention configuration provides benefit even for the detection of diffuse radiation because the contributions of inhomogeneities near the edges of the observed areas will be more evenly sampled at all wavelengths. In addition, to the extent that the acceptance cones, tissue thickness, and tissue scattering parameters can be chosen to include predominantly unscattered collimated light reaching the detectors, the variation of that detected light with analyte concentration will trend from the inherently complex form in equation [2] to the inherently more readily calibratable form of equation [1].

Figure 3C:
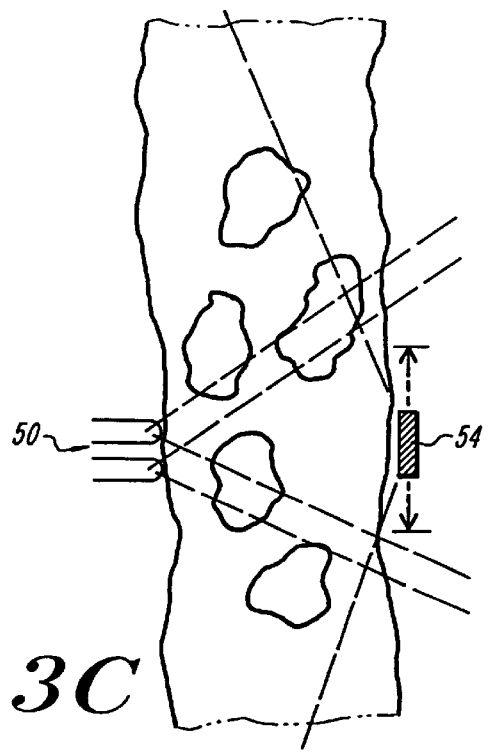
FIG. 3C shows the angular divergences typically employed in commercial pulse oximeters with a modification of the present invention shown.

FIG. 3C illustrates the optical geometry employed in most commercial pulse oximeters. Here, LEDs (50) at the selected wavelengths are placed adjacent to each other on one side of the tissue, and emit their radiation into the tissue at angles similar to those of the previously described fiber optics. The detector is placed on the far side of the monitored tissue, with an acceptance cone for light leaving the tissue that can approach the full hemisphere. Again, scattering spreads the light sideways about each incident ray, and light which the detectors receive will have sampled a region much wider than the spacing between the two detectors. This light includes contributions from tissue inhomogeneities which lie at the outer edges of the indicated rays, and since the degree of spreading is wavelength dependent, these inhomogeneities make different contributions to the signal at each wavelength. This effect is a major contributor to the high sensitivity of pulse oximetry results to motion of the site, compression of the site by the instrument, and to small changes in tissue thickness, all of which are greatly reduced in the present invention. To meet the present invention, detector 54 is broadened in area as shown by the dotted lines to be at least comparable in size to the sample thickness.

Figure 3E:
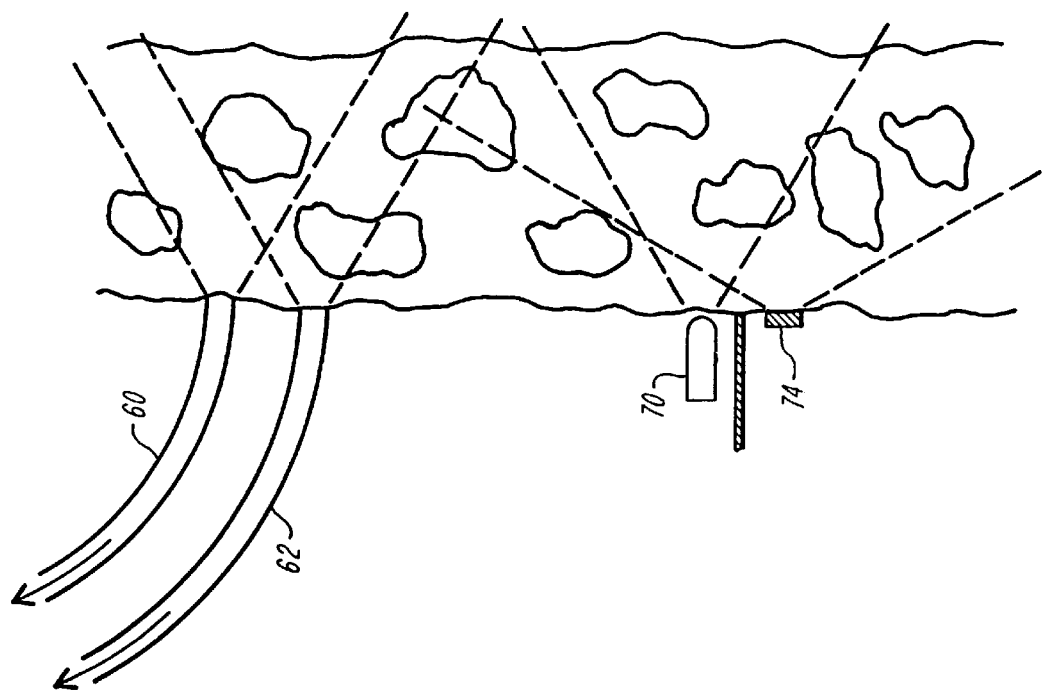
FIG. 3E shows two forms of the orientation used previously for the detection of reflected radiation.
Figure 3D:
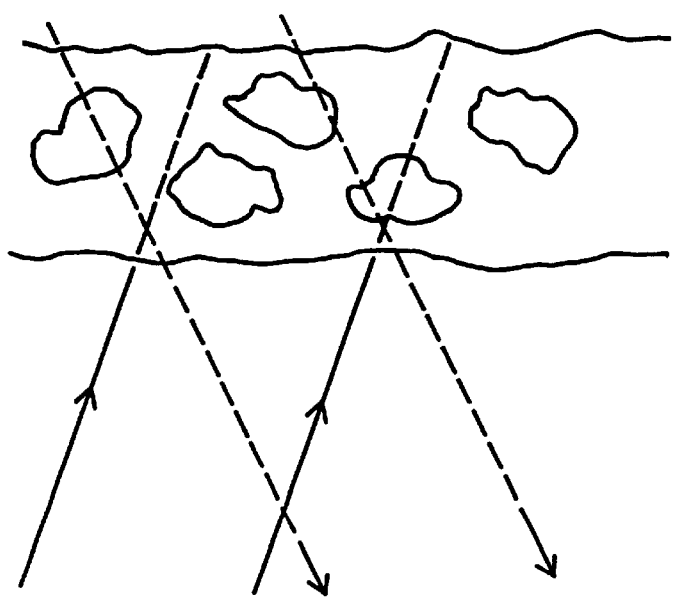
FIG. 3D shows the orientation an embodiment to detect reflected radiation from the scattering medium.

FIG. 3D illustrate the way in which the optical system of the present invention can be employed to detect radiation reflected or backscattered from the monitored site. This arrangement is particularly advantageous for sites such as the forehead or eyelid, where it is impractical to place a detector on the far side of the tissue. Here, the incident and emerging light beams preferably cross within the tissue. Once again, the advantage of this optical arrangement, even for detection of diffuse as opposed to singly scattered radiation, is that the relative contribution of tissue inhomogeneities near the edge of the illuminated area are rendered more equal between detectors at different wavelengths. The particular angles shown should be taken as illustrative rather than restrictive; there are numerous alternative arrangements well known in the art which provide additional advantages. One worthy of mention is the case in which the incident radiation would enter normal to the surface, with the restricted angle acceptance cones lying along (all or) part of an annulus centered about the incident beam.

FIG. 3E illustrates two optical configuration often employed in the prior art for the measurement of reflected light. The fiber optic (60/62) configuration shown suffers from the same limitations as that in FIG. 3B, with the wavelength dependent differences in scattering and hence penetration to deep inhomogeneities skewing the relative signal between detectors even more strongly. The 2nd configuration in FIG. 3E, with LEDs (70) and the detector (74) on the same side of the monitored site, has still greater potential for unequal sampling of both lateral and axial inhomogeneities because of the larger angular acceptance of the detector.

Although FIG. 2 shows a collimated beam for illuminating the tissue, in some circumstances it may be better for the illumination beam to be not perfectly collimated FIG. 4 shows two variations which implement such a non-collimated beam condition; FIG. 4A shows a converging beam for tissue illumination while FIG. 4B shows a slightly diverging beam for tissue illumination. More particularly, the apparatus of FIG. 4A has a radiation source 110 which generates a radiation beam that passes through a converging lens 112 before striking tissue 120. The focal point of converging lens 112 is on the opposite side of tissue 120 from radiation source 110. The radiation transmitted through tissue 120 passes through converging lens 132, preferably an aperture 134, and a recollimating lens 136.

FIG. 4B shows substantially the same system as FIG. 4A except lens 212 is a slightly diverging lens as a compared with the slightly converging lens 112 in FIG. 4A. Radiation source 210, lens 232, aperture 234 and lens 236 are the substantial equivalent of their corresponding numbered parts (110, 132, 134 and 136, respectively) in FIG. 4A. While FIGS. 4A and 4B illustrate an output beam from the optical system which is collimated, it may be that not all of optics 130 in FIG. 4A or optics 230 in FIG. 4B is necessary since a slight variation from collimation on the output beam may be desirable to get the best ratio of snakelike/ballistic to scattered rays. The configuration chosen is the one which empirically optimizes the transmitted photon intensity while maintaining insensitivity to internal inhomogeneities in the tissue.

Figure 5:
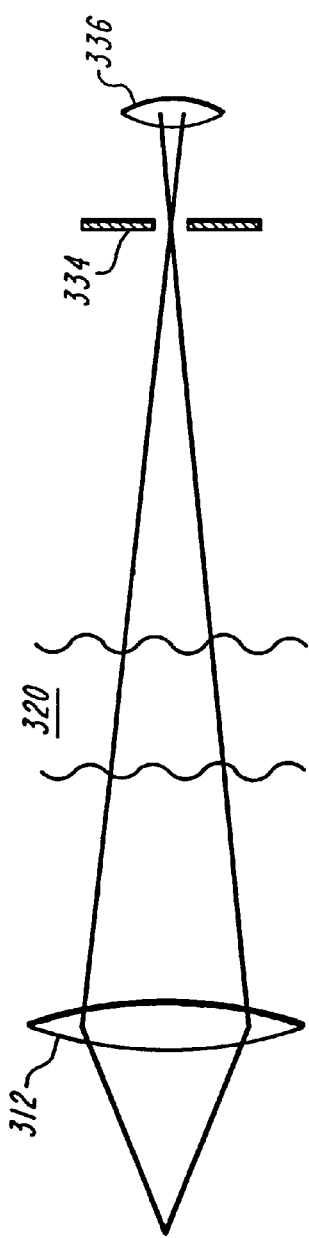
FIG. 5 shows an additional embodiment, a device with a converging lens and aperture placed near the focal point of the converging lens.

FIG. 5 shows another variation on the optical system of the invention, one with a more highly converging lens 312 which has a focal point on the far side of tissue 320. An aperture 334 is placed at or near the focal point of lens 312 and a recollimating lens 336 is placed near aperture 334. By placing aperture 334 at the focal point of lens 312, a pinhole camera-type system is created whereby the image of tissue 320 is reversed but formed directly upon the detector. Again, this optical system may have advantageous properties depending on the type of tissue or other sample measured.

FIG. 6 shows a variation of FIG. 2, whereby instead of the beam splitter apparatus 40 shown in FIG. 2, a bifurcated optical bundle which is split into four parts, each leading to a different detector unit, is substituted. If the detector units are located such that the length of the optical fiber leading to the particular detector unit is identical, this system provides an approximation of the congruent sampling shown in FIG. 2. More details concerning this type of bifurcated optical bundle is described in U.S. patent application Ser. No. 08/130,257.

Figure 7:
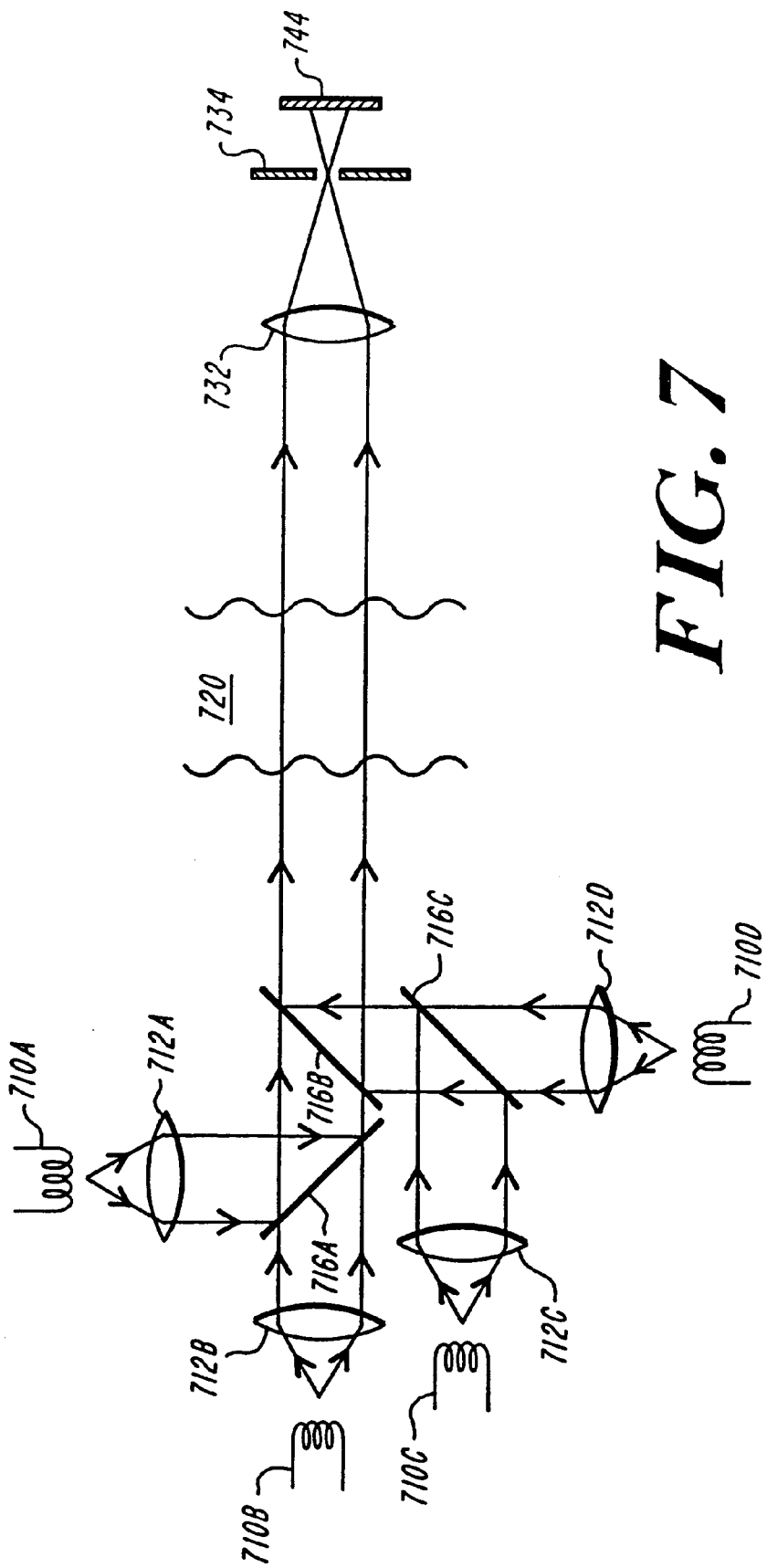
FIG. 7 shows a path reversed version of the optical system of FIG. 2, showing congruent illumination and collimated beams.

FIG. 7 shows a system using the beam splitter array of FIG. 2 reversed for congruent illumination rather than congruent sampling. Four radiation sources 710A, 710B, 710C and 710D, are used to illuminate the tissue sample. The radiation issuing from each of the radiation sources goes through a collimating lens (712A, 712B, 712C and 712D, respectively) and then is redirected by one of the beam splitters 716A, 716B or 716C to illuminate tissue 720. The radiation transmitted by tissue 720 passes through converging lens 732 and aperture 734 before striking detector 744. Optionally, an additional lens 736 (not shown) could be used to recollimate the transmitted radiation before it strikes detector 744. The radiation sources, collimating lenses and beam splitters are arranged to provide congruent illumination and each separate radiation source may have an associated modulator to provide a different modulation to the radiation issuing from that radiation source. This type of modulation apparatus, and its advantages, is described in more detail in U.S. patent application Ser. No. 08/182,572. Briefly, using a plurality of modulators each providing a different modulation to the associated radiation issuing therefrom, and using a form of modulation differentiation at the detector (such as electronically separating the signals based on modulation frequency) provides a method which allows differentiation at the detector of the source of the illuminating radiation, and accordingly allows additional information to be generated from a single detector. For example, if the radiation sources cover different wavelengths, a single detector can differentiate the intensity of the transmitted radiation at each wavelength range by using the modulation to determine the wavelength range. This can eliminate the requirement of the system illustrated above which requires a plurality of detector units. For improved results, both the congruent illumination shown in FIG. 7 and the congruent sampling shown in FIG. 2 may be used in the same device.

Figure 8:
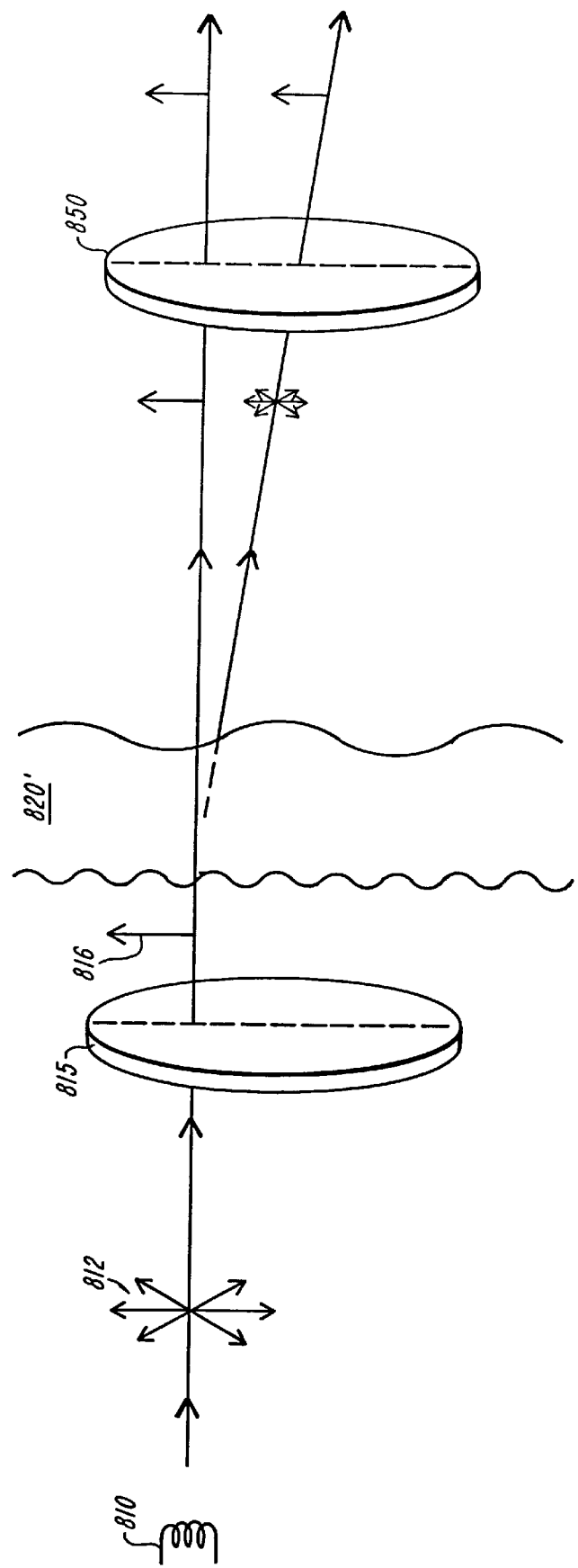
FIG. 8 shows a polarizer and analyzer system.

FIG. 8 shows a different embodiment of the invention whereby a polarizer and an analyzer are used in conjunction with the optical system in the invention to provide signal differentiation. More particularly, radiation source 810 emits radiation (shown with the polarization distribution 812) which then passes through polarizer 815. Only polarized radiation (see 816) illuminates tissue 820 and since the act of diffuse scattering in tissue 820 will depolarize the scattered light, only unscattered (or forward scattered) radiation is transmitted from tissue 820 as polarized radiation. The radiation is then transmitted through analyzer 850, which is a polarizer that passes only radiation which has the same polarization as polarizer 815, and detector 844 (not shown) detects this polarized radiation to yield a signal.

One advantage of using this polarizer/analyzer system is that it immediately segregates scattered from unscattered radiation, since scattered radiation is depolarized and cannot pass through analyzer 850 to detector 844. Accordingly, although collimation optics and the restricted solid angle can be used with the apparatus of FIG. 8, these are not absolutely necessary because the polarizer/analyzer pair will eliminate the off-angle scattered radiation in any case.

In all of the foregoing embodiments, there is an advantage to using geometrically broad beam radiation as opposed to narrow beam radiation. The use of such broad beam radiation provides a higher input signal which, when constrained by the solid angle restrictions of the present apparatus, still provides sufficient illumination and signal to meet the precision requirements for the analysis of trace constituents. Further, once the signals have been received, the processing described in the Block '265 Patent and the previously cited applications may be applied to differentiate signal from background and obtain meaningful data.

The advantages of the present invention apply to spectrophotometric systems such as those employed in pulse oximetry. While the shot-noise constraints on the detected intensity are lower because the absorption of the hemoglobins are so much larger the acceptance angle restrictions provide greater linearity and improved calibratability, as well as reduction in the severity of motion and breathing artifacts, and other limitations on universality of calibration.

For the analysis of trace constituents where the high photon flux requirement is critical, the present invention is particularly advantageous when combined with the use of broadband and broadband overlapping detectors, as taught in the Block '265 Patent and the parent applications.

The foregoing description is meant to be explanatory only and is not intended to be limiting as to the scope of the invention. The invention is defined by the following claims.

What is claimed is:

1. A device for imaging inhomogeneities in a tissue comprising:
   a radiation source for illuminating a designated area of said tissue with radiation having a wavelength between 700–2500 nm, said designated area being at least comparable in size to the thickness of said tissue, said illumination of said designated area being over a restricted solid angle;
   a detector comprising a plurality of detector units in an array, said detector arranged to receive radiation from only a limited solid angle with an area comparable in size to said designated area;

whereby a shadowgram of said inhomogeneities in said tissue is generated.

2. The device of claim 1 further comprising scanning means for scanning said radiation source and/or said detector across said tissue.

3. The device of claim 1 wherein said inhomogeneities comprise temperature inhomogeneities.

4. The device of claim 1 wherein said inhomogeneities comprise concentration inhomogeneities.

5. The device of claim 1 wherein said inhomogeneities comprise scattering inhomogeneities.

6. A method of imaging inhomogeneities in a tissue comprising:

illuminating a designated area of said tissue with a radiation source generating radiation having a wavelength between 700–2500 nm, said designated area being at least comparable in size to the thickness of said tissue, said illumination of said designated area being over a restricted solid angle;

detecting transmitted radiation with a detector comprising a plurality of detector units in an array, said detector arranged to receive radiation from only a limited solid angle with an area comparable in size to said designated area;

whereby a shadowgram of said inhomogeneities in said tissue is generated.

7. The method of claim 6 further comprising the step of using a scanning device to scan said radiation source and/or said detector across said tissue.

8. The method of claim 6 comprising the step of measuring temperature inhomogeneities by comparing said detected inhomogeneities with a temperature standard.

9. The method of claim 6 comprising the step of measuring concentration inhomogeneities by comparing said detected inhomogeneities with a concentration standard.

10. The method of claim 6 comprising the step of measuring scattering inhomogeneities by detecting inhomogeneities at various angles.

* * * * *